United States Patent [19]

Grollier et al.

[11] Patent Number: 4,842,849

[45] Date of Patent: Jun. 27, 1989

[54] COMPOSITION INTENDED FOR THE TREATMENT OF KERATIN FIBRES, BASED ON A CATIONIC POLYMER AND AN ANIONIC POLYMER CONTAINING VINYLSULPHONIC GROUPS

[75] Inventors: Jean F. Grollier; Claire Fiquet; Chantal Fourcadier, all of Paris; Claude Dubief, Versailles; Jean Mondet, Drancy; Daniele Cauwet, Crosne, all of France

[73] Assignee: L'Oreal, Paris, France

[21] Appl. No.: 115,612

[22] Filed: Oct. 30, 1987

Related U.S. Application Data

[63] Continuation of Ser. No. 376,036, May 7, 1982, abandoned.

[30] Foreign Application Priority Data

May 8, 1981 [LU] Luxembourg ............ 83.350

[51] Int. Cl.$^4$ .............................................. A61K 7/06
[52] U.S. Cl. ..................................... 424/70; 424/78; 424/DIG. 2; 8/405
[58] Field of Search .................. 424/70, DIG. 2, 78

[56] References Cited

U.S. PATENT DOCUMENTS

| | | | |
|---|---|---|---|
| 2,261,002 | 10/1941 | Ritter | 544/78 |
| 2,271,378 | 1/1942 | Searle | 424/250 |
| 2,273,780 | 2/1942 | Dittmar | 524/272 |
| 2,375,853 | 5/1945 | Kirby et al. | 564/295 |
| 2,388,614 | 11/1945 | Kirby et al. | 424/64 |
| 2,454,547 | 11/1948 | Bock et al. | 564/292 |
| 2,961,347 | 11/1960 | Floyd | 428/254 |
| 2,961,431 | 11/1960 | Kutner | 132/7 |
| 3,206,462 | 9/1965 | McCarty | 260/256.4 |
| 3,227,615 | 1/1966 | Korden | 132/7 |
| 3,429,963 | 2/1969 | Shedlovsky | 424/56 |
| 3,432,454 | 3/1969 | Hibbard | 424/78 |
| 3,472,243 | 10/1969 | Wall et al. | 424/70 |
| 3,472,604 | 10/1969 | Dasher et al. | 424/70 |
| 3,589,978 | 6/1971 | Kamal et al. | 162/158 |
| 3,836,537 | 9/1974 | Boerwinkle et al. | 132/7 |
| 3,874,870 | 4/1975 | Green et al. | 526/294 |
| 3,929,990 | 12/1975 | Green et al. | 424/78 |
| 3,966,904 | 6/1976 | Green et al. | 424/78 |
| 4,001,432 | 1/1977 | Green et al. | 424/329 |
| 4,005,193 | 1/1977 | Green et al. | 424/168 |
| 4,025,617 | 5/1977 | Green et al. | 424/78 |
| 4,025,627 | 5/1977 | Green et al. | 424/248.4 |
| 4,025,653 | 5/1977 | Green et al. | 424/325 |
| 4,026,945 | 5/1977 | Green et al. | 424/78 |
| 4,027,020 | 5/1977 | Green et al. | 424/248.56 |
| 4,031,307 | 6/1977 | De Martino et al. | 536/114 |
| 4,065,414 | 12/1977 | Seita et al. | 260/17 R |
| 4,066,827 | 1/1978 | Seita et al. | 526/50 |
| 4,119,590 | 10/1978 | Seita et al. | 260/8 |
| 4,131,576 | 12/1978 | Iovine et al. | 260/17.4 |
| 4,138,472 | 2/1979 | Neubauer et al. | 423/549 |
| 4,138,477 | 2/1979 | Gaffar | 424/81 |
| 4,185,087 | 1/1980 | Morlino | 424/70 |
| 4,240,450 | 12/1980 | Grollier et al. | 424/70 |
| 4,299,817 | 11/1981 | Hannan, III et al. | 424/70 |
| 4,358,286 | 11/1982 | Grollier et al. | 8/429 |
| 4,371,517 | 2/1983 | vanlerberghe et al. | 424/70 |

FOREIGN PATENT DOCUMENTS

| | | |
|---|---|---|
| 3044754 | 6/1981 | Fed. Rep. of Germany . |
| 2238474 | 2/1975 | France . |
| 2383660 | 10/1978 | France . |
| 2486394 | 1/1982 | France . |
| 951496 | 3/1964 | United Kingdom . |
| 1093986 | 12/1967 | United Kingdom . |
| 1187122 | 4/1970 | United Kingdom . |
| 1187124 | 4/1970 | United Kingdom . |
| 1188183 | 4/1970 | United Kingdom . |
| 1367238 | 9/1974 | United Kingdom . |
| 1455167 | 11/1976 | United Kingdom . |
| 1463175 | 2/1977 | United Kingdom . |
| 2039938 | 8/1980 | United Kingdom . |
| 2088209 | 6/1982 | United Kingdom . |

Primary Examiner—Leonard Schenkman
Attorney, Agent, or Firm—Fleit, Jacobson, Cohn & Price

[57] ABSTRACT

The treatment of keratin substances is described which comprises applying thereto at least one polymer containing one or more cationic groups in combination with an anionic polymer containing vinylsulphonic units of the formula:

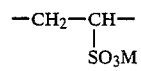

in which M denotes hydrogen, an alkali metal or alkaline earth metal or an ammonium or amine group, this anionic polymer optionally containing units derived from one or more cosmetically acceptable comonomers.

22 Claims, No Drawings

COMPOSITION INTENDED FOR THE TREATMENT OF KERATIN FIBRES, BASED ON A CATIONIC POLYMER AND AN ANIONIC POLYMER CONTAINING VINYLSULPHONIC GROUPS

This application is a continuation of application Ser. No. 376,036, filed May 7, 1982, now abandoned.

The present invention relates to compositions based on polymers, which are intended for use in the treatment of keratin substances and more particularly in the treatment of hair, the skin and the nails.

The use of compositions based on cationic polymers and anionic polymers for the treatment of keratin substances has already been described in U.S. Pat. No. 4,240,450. These compositions make it possible, in particular, to obtain an easy comb-out and a pleasant feel of the hair when wet and shine, hold and volume of the hair when dry.

The cationic polymers which are more particularly used contain primary, secondary, tertiary and/or quaternary amine groups and have a molecular weight of 500 to 5,000,000; the anionic polymers which could be used contain, in particular, sulphonic, carboxylic or phosphoric groups and have a molecular weight of 500 to 2,000,000.

We have discovered that polymers containing vinylsulphonic groups are particularly advantageous because of the properties which they make it possible to provide when these polymers are associated with polymers containing cationic groups, in particular as regards the comb-out, the stiffness or the hold of the hair and the softness to the touch, in particular on sensitised hair.

These polymers are more particularly polymers containing vinylsulphonic units.

The use of the polymers containing cationic groups in association with polymers containing vinylsulphonic units not only makes it possible to obtain the properties already mentioned above, but also makes it possible to reduce or overcome the disadvantages associated with the use of the sulphonic polymers more particularly mentioned in the abovementioned specification. In fact, although sulphonic polymers, such as polystyrenesulphonates or lignosulphonates, are advantageous when used in association with the cationic polymers, they have the disadvantage of making sensitised hair a little too rough and, furthermore, they frequently make it necessary to operate at rather high pH values in order to obtain clear solutions.

We have discovered, surprisingly, that the use of polymers containing vinylsulphonic units as anionic polymers makes it possible to obtain, on sensitised hair, a soft feel which is substantially free of roughness. The association of the cationic polymers with a polymer containing vinylsulphonic units also makes it possible, surprisingly, to have a better comb-out than with the other sulphonic polymers.

The use of the polymers containing vinylsulphonic units, according to the invention, also makes it possible, for a given composition, to obtain a clear composition at a pH below that at which this was possible for the same composition containing, for example, a polystyrenesulphonate as disclosed in the French Specification.

This possibility of lowering the pH for certain compositions can be advantageous, in particular from the point of view of harmlessness in the case of compositions intended for regular application to the skin, such as shampoos, rinsing compositions and lotions.

The present invention thus provides a process for the treatment of keratin substances which comprises using a cationic polymer, and an anionic polymer containing vinylsulphonic units, as well as a composition comprising these polymers.

The process according to the invention is essentially characterised in that at least one polymer containing cationic groups and at least one anionic polymer containing at least some vinylsulphonic units, of the formula:

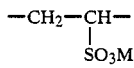

in which M denotes hydrogen, alkali metal or alkaline earth metal, an ammonium group or an amine group, are applied to the keratin substance in order to condition the said substance.

The process according to the invention applies more particularly to the treatment of the hair, in particular human hair, and also to the treatment of the skin and the nails, but can also apply to the treatment of keratin substances such as wool.

The anionic polymers which are more particularly used according to the invention are polyvinylsulphonates having a molecular weight of 1,000 to 100,000 and preferably of 2,000 to 25,000.

The salts preferably used within the scope of the invention are the sodium, potassium, calcium and ammonium salts and the organic amine salts, such as the alkylamine and alkanolamine salts, amongst which are preferred the salts of mono-, di- or tri-ethylamine, mono-, di- or tri-propylamine, isopropylamine, mono-, di- or tri-ethanolamine, 2-amino-2-methylpropane-1,3-diol and 2-amino-2-methylpropanol.

Copolymers containing vinylsulphonic groups with one or more cosmetically acceptable comonomers can also be used according to the invention. As comonomers which can be used, there may be mentioned unsaturated acids, such as acrylic or methacrylic acid, and their esters and amides, such as substituted or unsubstituted acrylamide or methacrylamide, vinyl esters, vinyl ethers and vinylpyrrolidone.

These polymers containing the vinylsulphonic group are described more particularly in U.S. Pat. Nos. 2,961,431 and 4,138,477 and French Pat. No. 2,238,474.

The polymers containing cationic groups which can be used according to the invention are polymers containing primary, secondary, tertiary and/or quaternary amine groups and have a molecular weight which is generally 1,000 to 5,000,000. Amongst these polymers, there may be mentioned (true) cationic polymers and amphoteric polymers.

The cationic polymers which are more particularly preferred according to the invention are especially:

(1) Vinylpyrrolidone/dialkylaminoalkyl acrylate or methacrylate copolymers (quaternised or unquaternised), such as those sold under the name Gafquat by the Gaf Corp, for example "copolymer 845" and Gafquat 734 or 755, described in greater detail in particular in French Pat. No. 2,077,143.

(2) Cellulose ether derivatives containing quaternary ammonium groups, such as those described in French Patent 1,492,597 and especially the polymers sold under the name JR, such as JR 125, JR 400 and JR 30 M, and under the name LR, such as LR 400 and LR 30 M, by the Union Carbide Corp., and cationic cellulose derivatives, such as the products sold under the names CELQUAT L 200 and CELQUAT H 100 by National Starch and described in U.S. Pat. No 4,131,576.

(3) Cationic polysaccharides, such as those described in U.S. Pats. 3 589 978 and 4 031 307, and in particular Jaguar C13 sold by MEYHALL.

(4) Cationic polymers chosen from:
(a) polymers containing units of the formula:

in which A denotes a radical containing two amino groups, preferably a piperazinyl radical, and Z denotes the symbol B or B'; B and B', which are identical or different, denote a divalent radical which is a straight-chain or branched-chain alkylene radical which contains up to, say, 7 consecutive carbon atoms in the main chain, is unsubstituted or substituted by one or more hydroxyl groups and can also contain one or more oxygen, nitrogen and sulphur atoms and 1 to 3 aromatic and/or heterocyclic rings, the oxygen, nitrogen and sulphur atoms generally being present in the form of an ether or thioether, sulphoxide, sulphone, sulphonium, amine, alkylamine, alkenylamine, benzylamine, amine oxide, quaternary ammonium, amide, imide, alcohol, ester and/or urethane group; these polymers and their preparation are described in French Patent 2 162 025;

(b) polymers containing units of the formula

in which A denotes a radical containing two amino groups, preferably a piperazinyl radical, and $Z_1$ denotes the symbol $B_1$ or $B'_1$ while denoting the symbol $B'_1$ at least once; $B_1$ denotes a divalent radical which is a straight-chain or branched-chain alkylene or hydroxyalkylene radical having up to, say, 7 consecutive carbon atoms in the main chain, and $B'_1$ is a divalent radical which is a straight-chain or branchedchain alkylene radical which has up to, say, 7 consecutive carbon atoms in the main chain, is unsubstituted or substituted by one or more hydroxyl radicals and is interrupted by one or more nitrogen atoms, the nitrogen atom being substituted by an alkyl chain which is optionally interrupted by an oxygen atom and optionally contains one or more hydroxyl groups; the polymers of the formula (II) and their preparation are described in French Pat. No. 2 280 361; and (c) the alkylation products, with alkyl and benzyl halides or lower (generally of 1 to 6 carbon atoms) alkyl tosylates or mesylates, and the oxidation products, of the polymers of the formulae (I) and (II) indicated above under (a) and (b).

(5) Optionally alkylated and crosslinked polyaminoamides chosen from at least one cross-linked polymer obtained by crosslinking a polyamino-polyamide (A) prepared by the polycondensation of an acid compound with a polyamine. The acid compound is chosen from (i) organic dicarboxylic acids, (ii) aliphatic monocarboxylic and dicarboxylic acids containing an ethylenic double bond, (iii) esters of the abovementioned acids, preferably the esters with lower alkanols having from 1 to 6 carbon atoms, and (iv) mixtures of these compounds. The polyamine is a bis-primary or mono- or bis-secondary polyalkylene-polyamine; up to 40 mol % of this polyamine can be replaced by a bis-primary amine, preferably ethylenediamine, or by a bis-secondary amine, preferably piperazine, and up to 20 mol % can be replaced by hexamethylenediamine. The crosslinking is carried out by means of a crosslinking agent (B) chosen from epihalogenohydrins, diepoxides, dianhydrides, unsaturated anhydrides and bis-unsaturated derivatives, in proportions of 0.025 to 0.35 mol of cross-linking agent per amine group of the polyamino-polyamide (A). These polymers and their preparation are described in greater detail in French Pat. No. 2,252,840.

The alkylation can be carried out with, say, glycidol, ethylene oxide, propylene oxide or acrylamide.

The optionally aklylated, crosslinked polyamino-polyamides do not contain a reactive group, do not have alkylating properties and are chemically stable.

The polyamino-polyamides (A) themselves can also be used according to the invention.

(6) Crosslinked polyamino-polyamides obtained by crosslinking a polyamino-polyamide (A, described above) by means of a crosslinking agent which is:

(I) compounds chosen from (1) bis-halogenohydrins, (2) bis-azetidinium compounds, (3) bis-halogenoacyldiamines and (4) bis-(alkyl halides);

(II) oligomers obtained by reacting a compound (a) chosen from the group comprising (1) bis-halogenohydrins, (2) bis-azetidinium compounds, (3) bis-halogenoacyl-di-amines, (4) bis-(alkyl halides), (5) epihalogenohydrins, (6) diepoxides and (7) bis-unsaturated derivatives, with a compound (b) which is a difunctional compound which is reactive towards the compound (a); and (III) the quaternisation product of a compound chosen from the compounds (I) and the oligomers (II) and containing one or more tertiary amine groups which can be totally or partially alkylated with an alkylating agent (c) preferably chosen from methyl or ethyl chlorides, bromides, iodides, sulphates, mesylates and tosylates, benzyl chloride or bromide, ethylene oxide, propylene oxide and glycidol, the crosslinking being carried out by means of 0.025 to 0.35 mol, in particular of 0.025 to 0.2 mol and more particularly of 0.025 to 0.1 mol, of crosslinking agent per amine group of the polyamino-polyamide.

These crosslinking agents and these polymers, together with the process for their preparation, are described in French Application No. 2,368,508.

(7) Polyamino-polyamide derivatives resulting from the condensation of a polyalkylene-polyamine with a polycarboxylic acid, followed by alkylation by means of difunctional agents. There may be mentioned the adipic acid/dialkylaminohydroxyalkyl-dialkylenetriamine copolymers in which the alkyl radical contains 1 to 4 carbon atoms and preferably denotes methyl, ethyl or propyl, which are described in French Pat. No. 1,583,363.

The products which make it possible to obtain particularly valuable results are the adipic acid/dimethylaminohydroxypropyl-diethylenetriamine copolymers sold under the name Cartaretine F, $F_4$ or $F_8$ by SANDOZ.

(8) Polymers obtained by reacting a polyalkylene-polyamine containing two primary amine groups and at least one secondary amine group, with a dicarboxylic acid chosen from diglycolic acid and saturated aliphatic dicarboxylic acids having 3 to 8 carbon atoms, the molar ratio of the polyalkylene-polyamine to the dicarboxylic acid being from 0.8:1 to 1.4:1, and the resulting polyamide being reacted with epichlorohydrin in a molar ratio of epichlorohydrin to the secondary amine groups of the polyamide of from 0.5:1 to 1.8:1; these polymers are mentioned in U.S. Pat. Nos. 3,227,615 and 2,961,347.

Particularly valuable polymers are those sold under the name HERCOSETT 57 by Hercules Incorporated, and under the name PD 170 or DELSETTE 101 by Hercules, in the case of the adipic acid/epoxypropyl-diethylenetriamine copolymer.

(9) Cyclic polymers generally having a molecular weight of 20,000 to 3,000,000, such as homopolymers containing, as the main constituent of the chain, units corresponding to the formula (III) or (III')

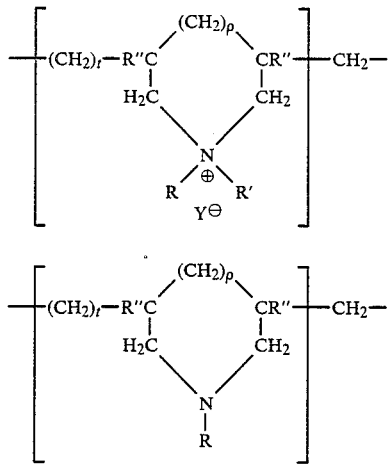

in which $p$ and $t$ are equal to 0 or 1, and $p+t=1$, R″ denotes hydrogen or methyl, R and R' independently of one another denote an alkyl group having 1 to 22 carbon atoms, a hydroxyalkyl group in which the alkyl group preferably has 1 to 5 carbon atoms, or a lower amidoalkyl group, and R and R' can denote, together with the nitrogen atom to which they are attached, heterocyclic groups such as piperidinyl or morpholinyl, and $Y^\ominus$ is an anion, such as bromide, chloride, acetate, borate, citrate, tartrate, bisulphate, bisulphite, sulphate or phosphate, and also copolymers containing units of the formula III or III' and, preferably, units derived from acrylamide or from diacetoneacrylamide. Amongst the quaternary ammonium polymers of the type defined above, those which are more particularly preferred are the dimethyldiallylammonium chloride homopolymer sold under the name MERQUAT 100 and having a molecular weight of less than 100,000, and the dimethyldiallylammonium chloride/acrylamide copolymer having a molecular weight of more than 500,000 and sold under the name MERQUAT 550 by MERCK.

These polymers are described in French Pat. No. 2,080,759 and its certificate of addition No. 2,190,406.

(10) Poly-(quaternary ammonium) compounds of the formula

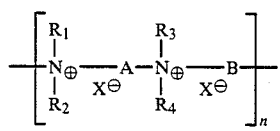

in which $R_1$ and $R_2$, and $R_3$ and $R_4$, which are identical or different, represent aliphatic, alicyclic or arylaliphatic radicals containing a maximum of 20 carbon atoms, or lower hydroxyaliphatic radicals, or alternatively $R_1$ and $R_2$, and $R_3$ and $R_4$, together or separately form, with the nitrogen atoms to which they are attached, heterocyclic rings optionally containing a second hetero-atom other than nitrogen, or alternatively $R_1$, $R_2$, $R_3$ and $R_4$ represent a group

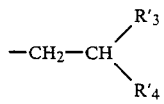

$R'_3$ denoting hydrogen or lower alkyl and $R'_4$ denoting

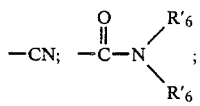

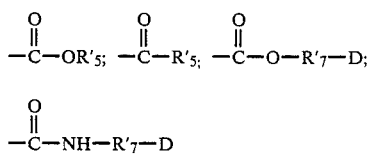

$R'_5$ denoting lower alkyl, $R'_6$ denoting hydrogen or lower alkyl, $R'_7$ denoting alkylene and D denoting a quaternary ammonium group; A and B independently represent a polymethylene group containing from 2 to 20 carbon atoms, which can be linear or branched and saturated or unsaturated and can contain, inserted in the main chain, one or more aromatic rings, such as the group

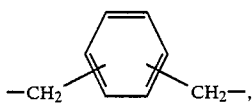

or one or more groups —CH$_2$—Y—CH$_2$—, Y denoting O, S, SO, SO$_2$, —S—S—,

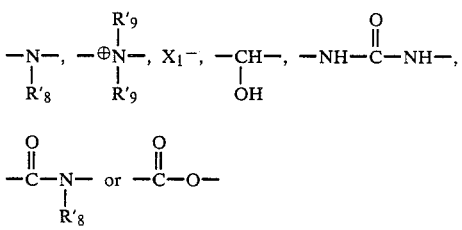

$X_1^-$ denoting an anion derived from a mineral or organic acid, $R'_8$ denoting hydrogen or lower alkyl and $R'_9$ denoting lower alkyl, or alternatively A and $R_1$ and $R_3$ form a piperazine ring with the two nitrogen atoms to which they are attached; moreover, if A denotes a linear or branched, saturated or unsaturated alkylene or hydroxyalkylene radical, B can also denote a group:

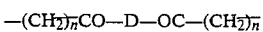

in which D denotes:

(a) a glycol radical of the formula —O—Z—O—, in which Z denotes a linear or branched hydrocarbon radical or a group corresponding to the formulae —[CH$_2$—CH$_2$—O]$_x$CH$_2$—CH$_2$— or

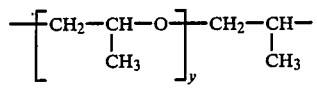

in which x and y denote an integer from 1 to 4, representing a definite and unique degree of polymerisation (or any number from 1 to 4, representing an average degree of polymerisation in the case of a mixture);

(b) a bis-secondary diamine radical, such as a piperazine derivative;

(c) a bis-primary diamine radical of the formula: —NH—Y—NH—, in which Y denotes a linear or branched hydrocarbon radical or the divalent radical —CH$_2$—CH$_2$—S—S—CH$_2$—CH$_2$—; or (d) a ureylene group of the formula —NH—CO—NH—;

n is such that the molecular weight is generally between 1,000 and 100,000; and X$^-$ denotes an anion.

Polymers of this type are described, in particular, in French Pat. Nos. 2,320,330, 2,270,846, 2,316,271, 2,336,434 and 2,413,907 and U.S. Pat. Nos. 2,273,780, 2,375,853, 2,388,614, 2,454,547, 3,206,462, 3,261,002 and 2,271,378.

Other polymers of this type are described in U.S. Pat. Nos. 3,874,870, 4,001,432, 3,929,990, 3,966,904, 4,005,193, 4,025,617, 4,025,627, 4,025,653, 4,026,945 and 4,027,020.

(11) Homopolymers or copolymers derived from acrylic or methacrylic acid and containing at least some units:

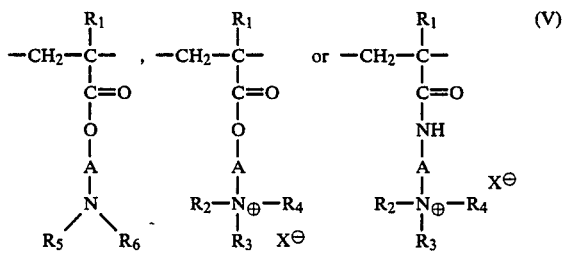

in which R$_1$ is H or CH$_3$, A is a linear or branched alkyl group having 1 to 6 carbon atoms or a hydroxyalkyl group having 1 to 4 carbon atoms, R$_2$, R$_3$ and R$_4$, which are identical or different, denote an alkyl group having 1 to 18 carbon atoms or a benzyl group, R$_5$ and R$_6$ denote H or alkyl having 1 to 6 carbon atoms and X denotes methosulphate or halide such as chloride or bromide.

The comonomer or comonomers which can be used typically belong to the family comprising: acrylamide, methacrylamide, diacetone-acrylamide, acrylamide and methacrylamide substituted on the nitrogen by one or more lower alkyl groups, alkyl esters of acrylic and methacrylic acids, vinylpyrrolidone and vinyl esters.

By way of example, there may be mentioned:

the products listed under the names Quaternium 38, 37, 49 and 42 in the Cosmetic Ingredient Dictionary, the acrylamide/beta-methacryloyloxyethyl-trimethylammonium methosulphate copolymers sold under the names Reten 205, 210, 220 and 240 by Hercules, the aminoethylacrylate phosphate/acrylate copolymer sold under the name Catrex by National Starch, and the crosslinked graft cationic copolymers having a molecular weight of 10,000 to 1,000,000, and preferably of 15,000 to 500,000, and resulting from the copolymerisation of:

(a) at least one cosmetic monomer,
(b) dimethylaminoethyl methacrylate,
(c) polyethylene glycol and
(d) a polyunsaturated crosslinking agent, These copolymers being described in French Pat. No. 2,189,434.

(12) Quaternary polymers of vinylpyrrolidone and of vinylimidazole, such as, LUVIQUAT FC 905 sold by BASF.

(13) Cationic silicone polymers, such as those described in European Applications 17,121 and 17,122, U.S. Pat No. 4,185,087, Japanese Patent Application 80/66,506 and Austrian Patent Application 71/01,171, or also those mentioned in the CTFA dictionary under the name MODIMETHICONE, such as the product marketed as a mixture with other ingredients under the name "Dow Corning 929" cationic emulsion.

Other cationic polymers which can be used as polyalkyleneimines, in particular polyethyleneimines, polymers containing vinylpyridine units or vinylpyridinium units in the chain, condensates of polyamines and of epichlorohydrin, poly-(quaternary ureylenes) and chitin derivatives.

The associations which are more particularly preferred according to the invention are associations with the cationic polymers of groups 1, 2, 4, 5, 6, 9, 10, 12 and 13.

It is also possible, according to the invention, to use amphoteric polymers in place of the true cationic polymers, the said amphoteric polymers performing the same function as the true cationics when they are associated with the anionic polymers used according to the invention.

The amphoteric polymers consist of units A and B randomly distributed in the polymer chain, in which A denotes a unit derived from a monomer containing at least one basic nitrogen atom and B denotes a unit derived from an acid monomer containing one or more carboxylic or sulphonic acid groups, or alternatively A and B can denote groups derived from zwitterionic monomers of carboxybetaine; A and B can also denote a cationic polymer chain containing secondary, tertiary or quaternary amine groups, in which at least one of the amine groups carries a carboxylic or sulphonic acid group joined via a hydrocarbon radical, or alternatively A and B form part of a chain of a polymer containing an alpha,beta-dicarboxyethylene unit in which one of the carboxylic acid groups has been reacted with a polyamine containing one or more primary or secondary amine groups.

These amphoteric polymers are chosen more particularly from:

(1) Polymers resulting from the copolymerisation of a monomer derived from a vinyl compound carrying a carboxylic acid group, such as acrylic acid, methacrylic acid, maleic acid or alpha-chloroacrylic acid, with a basic monomer derived from a substituted vinyl compound containing at least one basic nitrogen atom, such as dialkylaminoalkyl methacrylates and acrylates and dialkylaminoalkly-methacrylamides and -acrylamides. Compounds of this type are described in U.S. Pat. No. 3,836,537.

(2) Polymers containing units derived from:

(a) at least one monomer chosen from acrylamides and methacrylamides substituted on the nitrogen by an alkyl radical, (b) at least one acid comonomer containing one or more reactive carboxylic acid groups, and (c) at least one basic comonomer, such as esters of acrylic and methacrylic acids, containing primary, secondary, tertiary and quaternary amine substituents, and the quaternisation product of dimethylaminoethyl methacrylate with dimethyl or diethyl sulphate.

(3) The crosslinked polyamino-polyamides described above under (5) and (6), partially or totally alkylated by reaction with acrylic acid, chloroacetic acid or an alkanesultone, and their salts described in the abovementioned patents.

(4) Polymers containing zwitterionic units of the formula:

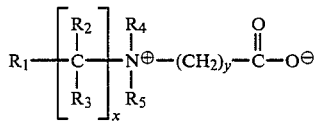

in which $R_1$ denotes a polymerisable unsaturated group, such as an acrylate, methacrylate, acrylamide or methacrylamide group, x and y represent an integer from 1 to 3, $R_2$ and $R_3$ represent hydrogen, methyl, ethyl or propyl and $R_4$ and $R_5$ represent a hydrogen atom or an alkyl radical such that the sum of the carbon atoms in $R_4$ and $R_5$ does not exceed 10.

The polymers containing such units can also contain units derived from non-zwitterionic monomers, such as vinylpyrrolidone, dimethylaminoethyl or diethylaminoethyl acrylate or methacrylate or alkyl acrylates or methacrylates, acrylamides or methacrylamides or vinyl acetate.

(5) Polymers derived from chitosan, containing monomeric units corresponding to the following formulae:

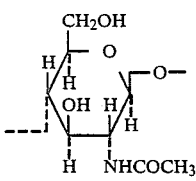

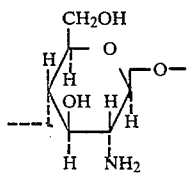

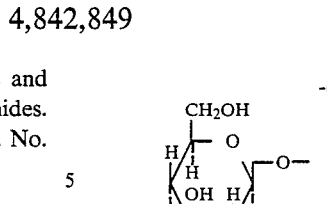

in which the unit A is present in an amount from 0 to 30%, B is present in an amount from 5 to 50% and C is present in an amount from 30 to 90%.

In formula C, R represents a radical of the formula:

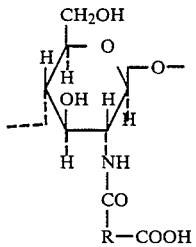

in which n is 0 or 1 such that if n=0, $R_6$, $R_7$ and $R_8$, which are identical or different, each represent a hydrogen atom, a methyl, hydroxyl, acetoxy or amino radical, a monoalkylamino radical or a dialkylamino radical, optionally interrupted by one or more nitrogen atoms and/or optionally substituted by one or more amine, hydroxyl, carboxyl, alkylthio or sulphonic acid groups, or an alkylthio radical in which the alkyl group carries an amino radical, at least one of the radicals $R_6$, $R_7$ and $R_8$ in this case being a hydrogen atom, or if n is equal to 1, $R_6$, $R_7$ and $R_8$ each represent a hydrogen atom, and also the salts formed by these compounds with bases or acids.

(6) The polymers containing units of the formula VII and described in French Pat. No. 1,400,366.

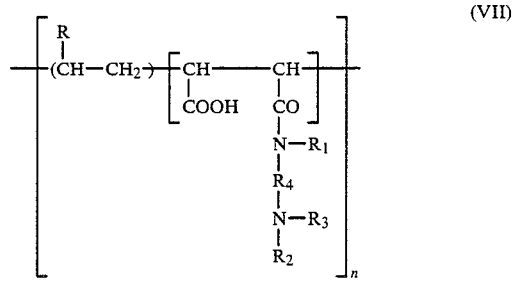

in which R represents a hydrogen atom or a $CH_3O$, $CH_3CH_2O$ or phenyl radical, $R_1$ denotes hydrogen or a lower alkyl radical, such as methyl or ethyl, $R_2$ denotes hydrogen or a lower alkyl radical, such as methyl or ethyl, and $R_3$ denotes a lower alkyl radical, such as methyl or ethyl, or a radical corresponding to the formula:

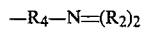

$R_4$ representing a group —$CH_2$—$CH_2$—, —$CH_2$—$CH_2$—$CH_2$,

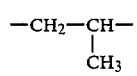

and also the upper homologues of these radicals containing up to 6 carbon atoms.

(7) Amphoteric polymers derived from the cationic polymers described under (4) above, and obtained by reacting chloroacetic acid or sodium chloroacetate with the said compounds.

(8) Amphoteric polymers of a betainised dialkylaminoalkyl (meth)acrylate or dialkylaminoalkyl-(meth)acrylamide, containing at least some units of the formula:

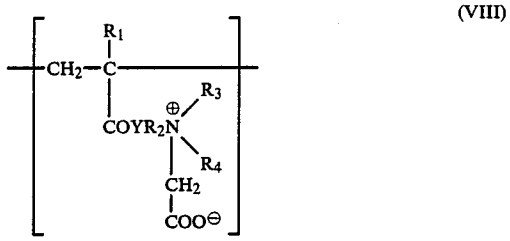

in which $R_1$ denotes a hydrogen atom or a methyl group, $R_2$ denotes an alkylene group having 1 to 4 carbon atoms, Y denotes O or —NH— and $R_3$ and $R_4$ independently of one another denote hydrogen or alkyl having 1 to 4 carbon atoms.

These polymers have a molecular weight of 1000 to 2,000,000.

The amphoteric polymers containing at least some units corresponding to the formula (VIII) above may be in the form of copolymers containing, in addition to the units of the formula (VIII) mentioned above, at least some units of the formula (IX)

in which $R_1$ has the same meaning as that indicated for the formula (VIII) and $R_5$ represents an alkyl or alkenyl radical having from 4 to 24 carbon atoms or a cycloalkyl radical having from 4 to 24 carbon atoms.

It is also possible to use ter-, tetra- or pentapolymers containing, in addition to the units (VIII) and (IX) defined above, units of the formula:

in which $R_6$ preferably denotes an alkyl or alkenyl group having 1 to 3 carbon atoms, $R_1$ having the same meaning as that indicated for the formula (VIII), and/or units derived from a hydrophilic ethylenic monomer (XI), and/or units of a second ethylenic monomer (XII) different from the abovementioned units.

The units of the formula (VIII) are preferably present in proportions of 25 to 45% by weight and the units of the formula (IX) are preferably present in proportions of 5 to 65% by weight.

The units of the formula (X) are preferably present in proportions up to 50% by weight, whilst the units (XI) and (XII) are present in proportions up to 20% by weight, relative to the total weight of the polymer.

A particularly preferred polymer is the copolymer containing units of the formulae (VIII), (IX) and (X) in which Y denotes an oxygen atom, $R_2$ denotes the group —$C_2H_4$—, $R_1$, $R_3$ and $R_4$ denote methyl, $R_5$ denotes an alkyl group having 4 to 18 carbon atoms and $R_6$ denotes an alkyl group having 1 to 3 carbon atoms, the average molecular weight of this polymer preferably being 70 000 to 90,000.

A particularly preferred embodiment of the invention consists in applying, to keratin fibres, the association of the anionic polymer containing vinylsulphonic groups with a cationic polymer, using a single composition. The invention thus provides the compositions used in this treatment process.

These compositions contain, in a medium permitting the application of the polymers to the fibres to be treated, the cationic polymers and the anionic polymers containing vinylsulphonic groups, typically in proportions of 0.01 to 10% by weight and preferably 0.1 to 5% by weight.

The pH of these compositions is generally 2 to 11 and preferably 3 to 10.

These compositions can be presented in various forms, such as a liquid, cream, emulsion, gel, thickening lotion or powder; they can contain water and also any cosmetically acceptable solvent, in particular monoalcohols, such as alkanols having 1 to 8 carbon atoms, like ethanol, isopropanol, benzyl alcohol and phenylethyl alcohol, polyalcohols, such as alkylene glycols, like ethylene glycol and propylene glycol, and glycol ethers, such as mono-, di- and tri-ethylene glycol monoalkyl ethers, for example ethylene glycol monomethyl ether, ethylene glycol monoethyl ether and diethylene glycol monoethyl ether, used singly or in a mixture. These solvents can be present in proportions up to, say, 70% by weight, relative to the weight of the total composition.

These compositions can also be packaged as an aerosol, in which case they can be applied either in the form of an aerosol spray or in the form of an aerosol foam.

As the propellant gas for these aerosols, it is possible to use, in particular, carbon dioxide, nitrogen, nitrous oxide and volatile hydrocarbons, such as butane, isobutane, propane and, preferably, chlorinated and fluorinated hydrocarbons.

Preferred compositions can also contain electrolytes, such as alkali metal salts, like sodium, potassium or lithium salts, these salts preferably being halides, such as the chloride or bromide, and the sulphate, or salts with organic acids, such as the acetates or lactates, and also alkaline earth metal salts, preferably the carbonates, silicates, nitrates, acetates, gluconates, pantothenates and lactates of calcium, magnesium and strontium.

These compositions can also be presented in the form of a powder or of lyophilisates to be diluted before use.

The compositions according to the invention can contain any other ingredient normally used in cosmetics, such as perfumes, dyestuffs which can serve to colour the composition itself or the fibres, preservatives, sequestering agents, thickeners, silicones, softeners, foam synergistic agents, foam stabilisers, sun filters, peptising agents and also anionic, non-ionic, cationic or amphoteric surface-active agents or mixtures thereof.

These compositions can be used, in particular, in the form of a shampoo, a rinsing lotion, a cream or a treatment product which can be applied before or after colouring or bleaching, before or after shampooing, before or after perming or before or after straightening, and can also adopt the form of a colouring product, a setting lotion, a brushing lotion, a bleaching product, a perming product or a straightening product.

These compositions can also be used in the form of a cream, milk, emulsion, gel or lotion for the treatment of the skin, or in the form of lotions used for hardening the nails.

A particularly preferred embodiment consists of use in the form of a shampoo for washing the hair.

In this case, these compositions contain anionic, cationic, non-ionic or amphoteric surface-active agents typically in an amount from 3 to 50% by weight, preferably 3 to 20%, and their pH is 3 to 10.

A list of the surface-active agents which can be used according to the invention is given in French Patent Application No. 2 383 660, the disclosure of which is hereby incorporated by reference.

Another preferred embodiment consists of use in the form of a rinsing lotion to be applied mainly before or after shampooing. These lotions are typically aqueous or aqueousalcoholic solutions, emulsions, thickened lotions or gels. If the compositions are presented in the form of an emulsion, they can be non-ionic or anionic. The non-ionic emulsions consist mainly of a mixture of an oil and/or a fatty alcohol with a polyoxyethyleneated alcohol, such as polyoxyethyleneated stearyl or cetyl/stearyl alcohol, and cationic surface-active agents can be added to these compositions.

The anionic emulsions are formed essentially from soap.

If the compositions are presented in the form of a thickened lotion or a gel, they contain thickeners in the presence or absence of a solvent. The thickeners which can be used are especially sodium alginates, gum arabic and cellulose derivatives, and it is also possible to achieve thickening by means of a mixture of polyethylene glycol stearate or distearate or by means of a mixture of a phosphoric acid ester and an amide. The concentration of thickener is suitably 0.05 to 15% by weight. If the compositions are presented in the form of a styling lotion, shaping lotion or setting lotion, they generally comprise, in aqueous, alcoholic or aqueousalcoholic solution, the polymers defined above and also, if appropriate, non-ionic polymers.

If the compositions of the invention are intended for use in the dyeing of keratin fibres, and in particular human hair, they contain at least one oxidation dyestuff precursor and/or one direct dyestuff, in addition to the cationic polymer or polymers and the anionic polymer containing vinylsulphonic groups. They can also contain any other adjuvant normally used in this type of composition.

The pH of the dyeing compositions is generally 7 to 11 and can be adjusted to the desired value by adding an alkalising agent.

The composition according to the invention can also be used for waving or straightening the hair. In this case, the composition contains, in addition to the anionic polymer and the cationic polymer or polymers, one or more reducing agents and, if appropriate, other adjuvants normally used in this type of composition; such compositions are intended for use conjointly with a neutralising composition.

If the compositions are emulsions (milks or creams) intended for application to the skin, they contain, in addition to the cationic polymer or polymers and the anionic polymer containing vinylsulphonic groups, oils of natural or synthetic origin, emulsifiers and water and, if appropriate, humectants, softeners, thickeners, U.V. filters, preservatives, perfumes or mineral fillers, for example.

Another embodiment of the process according to the invention can consist in forming the association of the cationic polymer with the anionic polymer containing vinylsulphonic groups on the fibres, and in particular on the hair, by applying, in a first stage, a composition presented, for example, in the form of a pre-lotion and containing the cationic polymer, and in a second stage, a composition, such as a shampoo or a dye, containing the anionic polymer with vinylsulphonic groups.

According to another embodiment of the invention, it is possible to apply, in a first stage, a shampoo containing the cationic polymer, and in a second stage, a composition, such as a lotion, containing the anionic polymer with vinylsulphonic groups.

Another possible procedure is to use a perming, straightening, colouring or bleaching composition containing the cationic polymer, and to follow the treatment with this first composition by a treatment with a composition containing the anionic polymer with vinylsulphonic groups, the latter being placed in a composition which can be a shampoo, an oxidising solution or a simple lotion.

Another possible procedure is successively to use a first shampoo containing the cationic polymer, and, in a second stage, a second shampoo containing the anionic polymer with vinylsulphonic groups, it being possible for the pH of the compositions applied in these two stages to be different and adjusted so that, at the time of application of the composition containing the anionic polymer with vinylsulphonic groups, it is under the conditions permitting a good deposition of the association according to the invention on the fibres to be treated.

The following Examples further illustrate the present invention.

EXAMPLE 1

The following composition is prepared:

| | |
|---|---|
| Sodium polyvinylsulphonate | 1 g |
| Sodium chloride | 4 g |
| Cationic polyamide-polyamine polymer sold, as an aqueous solution containing 30% of active ingredient, under the name CARTARETINE F8 by SANDOZ | 6 g |
| Alkyl($C_{12}$-$C_{18}$)-dimethylcarboxymethylammonium hydroxide containing 30% of active ingredient, sold under the name DEHYTON AB30 by HENKEL | 6 g |
| Surface-active agent of the formula: RCHOH—CH$_2$O[CH$_2$—CHOH—CH$_2$O]$_n$H R = $C_9$-$C_{12}$ alkyl n = 3.5, statistical value | 5 g |
| Nonylphenol oxyethyleneated with 9 mols of ethylene oxide, sold under the name ANTAROX CO 630 by GAF | 5 g |
| Sodium hydroxide q.s.p. pH | pH 7 |
| Perfume | |
| Preservative | |
| Dyestuff | |
| Water q.s p | 100 g |

This clear composition is used as a shampoo. Sensitised hair which is dirty and wet is impregnated and the formation of a mild foam is observed. After an interval of a few minutes, followed by rinsing, the wet hair is easy to comb out and is soft to the touch.

The dried hair is soft to the touch and easy to comb out.

On replacing the anionic polymer by sodium polystyrenesulphonate in the composition described above, the appearance of turbidity is observed and this only disappears when the pH is increased above 9.1.

The treated hair is rougher and is distinctly less easy to comb out than the hair treated with the composition based on sodium polyvinylsulphonate.

The sodium polyvinylsulphonate used in the examples has a molecular weight of about 4,300.

EXAMPLE 2

The following composition is prepared:

| | |
|---|---|
| Sodium polyvinylsulphonate | 0.9 g |
| Sodium chloride | 4.0 g |
| Quaternary polyvinylpyrrolidone copolymer having a molecular weight of 1,000,000 and containing 20% of active ingredient, marketed under the name GAFQUAT 755 by GENERAL ANILIN | 2.5 g |
| Glucoside alkyl ether containing 30% of active ingredient, sold under the name TRITON CG 100 by SEPPIC | 8.0 g |
| Lauryl alcohol polyoxyethyleneated with 12 mols of ethylene oxide | 12.0 g |
| Perfume | |
| Preservative | |
| Dyestuff | |
| Sodium hydroxide q.s.p. pH | 7.3 |
| Water q.s.p. | 100 g |

This composition is clear. When applied as a shampoo under the conditions of Example 1, similar results are observed.

On replacing the sodium polyvinylsulphonate by the same amount of sodium polystyrenesulphonate in this composition, turbidity is observed and this is only removed when the pH is brought above 9.

EXAMPLE 3

The following composition is prepared:

| | |
|---|---|
| Sodium polyvinylsulphonate | 0.3 g |
| Sodium chloride | 4.0 g |
| Dimethyldiallylammonium chloride/acrylamide copolymer having a molecular weight of 500,000 and containing 8% of active ingredient, sold under the name MERQUAT 550 by MERCK | 3.0 g |
| MIRANOL C 2M, a cycloimidazoline derivative of coconut oil, sold by MIRANOL | 6.0 g |

$$R-C\begin{matrix} \diagup CH_2-COONa \\ \overset{\oplus}{N} \\ \diagdown CH_2CH_2-CH_2-O-CH_2COO^{\ominus} \end{matrix}$$
$$\overset{\|}{N}\diagdown_{CH_2}$$

R = copra, containing 40% of active ingredient

| | | |
|---|---|---|
| Alkyl($C_{12}-C_{18}$)—dimethylcarboxymethylammonium hydroxide containing 30% of active ingredient, sold under the name DEHYTON AB 30 by HENKEL | | 10.0 g |
| Perfume | | |
| Preservative | | |
| Dyestuff | | |
| Hydrochloric acid | q.s.p. | pH 7.4 |
| Water | q.s.p. | 100.0 g |

In the same way as the compositions of Examples 1 and 2, this composition is used as a shampoo. The hair washed with this composition is easy to comb out and the dried hair is soft to the touch and easy to comb out.

On replacing the polyvinylsulphonate by sodium polystyrenesulphonate in this example, the formation of turbidity is observed and this is only removed when the pH is brought above 8.

Furthermore, hair treated with the composition based on sodium polystyrenesulphonate is distinctly rougher to the touch and is less easy to comb out than the hair treated with the composition containing sodium polyvinylsulphonate.

EXAMPLE 4

The following composition is prepared:

| | |
|---|---|
| Sodium polyvinylsulphonate | 2.0 g |
| Sodium chloride | 4.0 g |
| Quaternised cellulos sold under the name JR 400 by UNION CARBIDE | 0.8 g |
| Triethanolamine alkyl($C_{12}-C_{14}$)-sulphate containing 40% of active ingredient | 6.0 g |
| Akypo RLM 100, which is a product of the formula R—(OCH$_2$CH$_2$)$_{10}$OCH$_2$COOH R being a mixture of $C_{12}-C_{14}$ alkyl radicals, containing 90% of active ingredient, sold by CHEM Y | 15.0 g |
| Perfume | |
| Preservative | |
| Dyestuff | |
| Sodium hydroxide q.s.p. pH | 7.8 |
| Water q.s.p. | 100.0 g |

On using this composition as a shampoo, the results observed are similar to those observed for the first three examples.

On replacing the sodium polyvinylsulpdhonate by sodium polystyrenesulphonate in this case as well, turbidity is found and this is only removed when the pH is brought above 9.

EXAMPLE 5

The following composition is prepared:

| | |
|---|---|
| Sodium polyvinylsulphonate | 0.45 g |
| Sodium chloride | 4.0 g |
| Polymer resulting from the polycondensation of equimolecular amounts of adipic acid and diethylenetriamine, followed by crosslinking with epichlorohydrin (11 mols of epichlorohydrin per 100 amine groups). | 0.91 g |
| Sodium salt of sulphated alkanol($C_{12}-C_{14}$) oxyethyleneated with 2.2 mols of ethylene oxide, containing 25% of active ingredient | 15.0 g |
| Triethanolamine salt of the condensation product of copra acids and animal protein hydrolysates, containing 40% of active ingredient, sold under the name MAYPON 4CT by STEPAN | 10.0 g |
| Decyldimethylamine oxide containing 30% of active ingredient, sold under the name BARLOX 10S by LONZA | 2.1 g |
| Hydrochloric acid q.s.p pH | 7.4 |
| Perfume | |
| Preservative | |
| Dyestuff | |
| Water q.s.p. | 100.0 g |

The composition obtained is clear.

When used as a shampoo, this composition imparts softness to the wet hair, and the dried hair is easy to comb out and soft to the touch and has a good hold.

EXAMPLE 6

The following compositions are prepared:

Composition A
Polymer of the formula

|  |  |
|---|---|
| $\left[ \begin{array}{cc} CH_3 & CH_3 \\ | & | \\ N^{\oplus}-(CH_2)_3 N^{\oplus}-(CH_2)_6 \\ | & | \\ CH_3 \; Cl^{\ominus} & CH_3 \; Cl^{\ominus} \end{array} \right]_n$ | 0.8 g |
| Sodium chloride | 4.0 g |
| Surface-active agent of the formula: RCHOH—CH$_2$O[CH$_2$—CHOH—CH$_2$O]$_n$H R = C$_9$-C$_{12}$ alkyl n = 3.5, statistical value | 15.0 g |
| Sodium hydroxide | q.s.p. pH 8 |
| Perfume |  |
| Preservative |  |
| Dyestuff |  |
| Water | q.s.p. 100.0 g |
| Composition B |  |
| Sodium polyvinylsulphonate | 1.2 g |
| Sodium hydroxide | q.s.p. pH 7.9 |
| Perfume |  |
| Preservative |  |
| Dyestuff |  |
| Water | q.s.p. 100.0 g |

The hair is washed with composition A, which is a clear shampoo, and then composition B is applied to the wet hair.

After an interval of a few minutes, the hair is rinsed with water and it is observed that the wet hair is easy to comb out and the dried hair is soft to the touch and easy to comb out and has a good hold.

EXAMPLE 7

The following composition is prepared:

|  |  |
|---|---|
| Sodium polyvinylsulphonate | 1.6 g |
| Sodium chloride | 4.0 g |
| Quaternary polyvinylpyrrolidone copolymer having a molecular weight of 1,000,000 and containing 20% of active ingredient, marketed under the name GAFQUAT 755 by GENERAL ANILIN | 3.0 g |
| Mixture of cetyl/stearyl alcohol and cetyl/stearyl alcohol oxyethyleneated with 12 mols of ethylene oxide, containing 100% of active ingredient, sold by HENKEL under the name SINNOWAX AO | 3.0 g |
| Oleyl alcohol | 1.0 g |
| Hydroxyethylcellulose sold by UNION CARBIDE under the name CELLOSIZE QP 4400 H | 0.5 g |
| Distearyldimethylammonium chloride | 0.4 g |
| Chlorhexidine dihydrochloride | 0.5 g |
| Sodium hydroxide q.s.p. pH | 8.2 |
| Perfume |  |
| Dyestuff |  |
| Water q.s.p. | 100.0 g |

This composition is applied after washing the hair with a shampoo. After an interval of 10 minutes, the hair is rinsed with running water.

The wet hair is soft to the touch and easy to comb out.

The dried hair is shiny, soft to the touch and easy to comb out.

EXAMPLE 8

The following composition is prepared:

|  |  |
|---|---|
| Sodium polyvinylsulphonate | 0.7 g |
| Sodium chloride | 4.0 g |
| Polyethyleneimine sold under the name POLYMIN P by BASF, as a 50% strength aqueous solution (d = 1.07, Brookfield viscosity: 10,000 to 20,000 cPo at 10° C. and 20 rpm) | 1.5 g |
| Hydrochloric acid q.s.p. pH | 8.6 |
| Perfume |  |
| Preservative |  |
| Dyestuff |  |
| Water q.s.p. | 100.0 g |

When applied under the same conditions as the composition of Example 7, similar results are observed.

EXAMPLE 9

The following composition is prepared:

|  |  |
|---|---|
| Sodium polyvinylsulphonate | 0.4 g |
| Product resulting from the polycondensation of epichlorohydrin and piperazine and having a molecular weight of 1,500 to 2,000, prepared in accordance with Example 1 of French Patent 2,162,025 | 1.0 g |
| Surface-active agent of the formula: RCHOH—CH$_2$O[CH$_2$—CHOH—CH$_2$O]$_n$H R = C$_9$-C$_{12}$ alkyl n = 3.5, statistical value | 1.0 g |
| Perfume |  |
| Preservative |  |
| Dyestuff |  |
| Hydrochloric acid q.s.p. pH | 7 |
| Water q.s.p. | 100.0 g |

This composition is packaged as an aerosol, using 8% of a 50/50 mixture of the propellants Freon 12 (dichlorodifluoromethane) and Freon 114 (dichlorotetrafluoroethane) and 92% of the above composition.

When applied from the aerosol pack, this composition is in the form of a foam, which disappears very rapidly on contact with the hair.

After an interval of a few minutes, the hair is rinsed and dried and it is observed that the hair is soft to the touch, has a good hold and is easy to comb out.

EXAMPLE 10

The following lotion is prepared:

|  |  |
|---|---|
| Celquat L200 | 0.5 g |
| Sodium polyvinylsulphonate | 0.5 g |
| Distearyldimethylammonium chloride | 0.3 g |
| Water q.s.p. 100 | g |

This composition is applied to clean hair.

After application of this composition, the dried hair is soft to the touch and easy to comb out and has a good hold.

EXAMPLE 11

The following composition is prepared:

|  |  |
|---|---|
| Vinylsulphonate/acrylamide copolymer (30%/70%) obtained by photopolymerisation | 0.5 g |
| Epichlorohydrin/piperazine polycondensate having a molecular weight of 1,500 to 2,000, prepared in accordance with Example 1 of French Patent 2,162,025 | 0.5 g |
| TRITON CG 110 | 40.0 g |
| Perfume |  |
| Preservative |  |
| Dyestuff |  |
| Hydrochloric acid q.s.p. pH | 8.8 |
| Water q.s.p. | 100.0 g |

When used as a shampoo, this composition imparts softness to the wet hair, and the dried hair is easy to comb out and has a good hold.

EXAMPLE 12

The following composition is prepared: Polymer formed from octylacrylamide, t-butylaminoethyl methacrylate and two (or more) monomers consisting of acrylic acid, methacrylic acid or their simple esters, sold under the name AMPHOMER M

| | |
|---|---|
| by National Starch | 1 g |
| Sodium polyvinylsulphonate | 0.7 g |
| Surface-active agent of the formula: RCHOH—CH$_2$O[CH$_2$CHOHCH$_2$O]$_n$H R = C$_9$–C$_{12}$ alkyl n = 3.5, statistical value | 8 g |
| MIRANOL C 2M | 5 g |
| Perfume | |
| Preservative | |
| Dyestuff | |
| Sodium hydroxide q.s.p. | pH = 6 |
| Water q.s.p. | 100 g |

When using this composition as a shampoo, the results observed are similar to those observed in Example 11.

EXAMPLE 13

The following composition is prepared:

| | |
|---|---|
| Sodium polyvinylsulphonate | 0.5 g |
| Gafquat 734 (quaternary polyvinylpyrrolidone copolymer having a molecular weight of 100,000, marketed by General Aniline) | 0.8 g of active ingredient |
| Ethyl alcohol q.s.p. | 50° strength |
| Perfume and dyestuff q.s. | |
| Water q.s.p. | 100 cc |

This composition is used as a lotion for conditioning human hair.

EXAMPLE 14

The following composition is prepared:

| | |
|---|---|
| Sodium polyvinylsulphonate | 0.4 g |
| Celquat L 200 | 0.5 g |
| Perfume, dyestuff and preservative q.s. | |
| Water q.s.p. | 100 cc |

This composition is used as a hair-conditioning lotion.

EXAMPLE 15

A shampoo having the following composition is prepared:

| | |
|---|---|
| Sodium and magnesium salt of sulphated oxyethyleneated lauryl alcohol, containing 30% of active ingredient, sold under the name TEXAPON ASV by HENKEL | 24 g |
| Trideceth-7 carboxylic acid of the formula: CH$_3$(CH$_2$)$_{11}$CH$_2$(OCH$_2$CH$_2$)$_6$OCH$_2$COOH sold by SANDOZ under the name SANDOPAN DTC acid | 5 g |
| Epichlorohydrin/piperazine polycondensate having a molecular weight of 1,500 to 2,000 (prepared according to example 1 of French patent 2,162,025) | 1 g of active ingredient |
| Sodium polyvinylsulphonate | 0.7 g of active ingredient |
| Sodium chloride | 4 g |
| Water, dyestuff, perfume, preservative q.s.p. | 100 g |
| pH = 7 with hydrochloric acid. | |

This composition imparts softness to the wet hair, and the dried hair is easy to comb out.

EXAMPLE 16

The shampoo having the following composition is prepared:

| | |
|---|---|
| Surface-active agent of the formula: R—CHOHCH$_2$O[CH$_2$CHOHCH$_2$O]$_n$H R = C$_9$–C$_{12}$ alkyl n = 3.5, statistical value | 10 g |
| Quaternary polymer containing vinylpyrrolidone units and vinylimidazole units, sold under the name LUVIQUAT FC 905 by B.A.S.F | 0.8 g of active ingredient |
| Na polyvinylsulphonate | 1.2 g of active ingredient |
| Sodium chloride | 4 g |
| Water, perfume, preservative, dyestuff q.s.p. | 100 g |
| pH = 7.3 with sodium hydroxide. | |

The results observed are similar to those of Example 15.

EXAMPLE 17

The shampoo having the following composition is prepared:

| | |
|---|---|
| Glucoside alkyl ether containing 30% of active ingredient, sold under the name TRITON CG 110 by SEPPIC | 30 g |
| Quaternised guar gum derivative sold under the name JAGUAR C 13 S by MEYHALL | 0.35 g of active ingredient |
| Na polyvinylsulphonate | 0.7 g of active ingredient |
| Sodium chloride | 4 g |
| Water, perfume, preservative, dyestuff q.s.p | 100 g |
| pH = 7.7 with sodium hydroxide. | |

The wet hair washed with the shampoo is soft to the touch and the dried hair is easy to comb out and has a good hold.

EXAMPLE 18

The rinsing lotion having the following composition is prepared:

| | |
|---|---|
| Cationic silicone polymer sold under the name CATIONIC EMULSION DC 929 by Dow Corning | 0.5 g of active ingredient |
| Na polyvinylsulphonate | 0.9 g of active ingredient |
| Na chloride | 4 g |
| Water, perfume, preservative, dyestuff q.s.p | 100 g |
| pH = 6.6 with sodium hydroxide. | |

Clean human hair, rinsed with this lotion, is easy to comb out and has a good hold.

EXAMPLE 19

The following oxidation dyeing composition is prepared:

| | |
|---|---|
| Triethanolamine lauryl-sulphate containing 40% of active ingredient | 2.5 g |
| 2-Octyldodecanol marketed under the name EUTANOL G by HENKEL | 7.5 g |
| Oleic diethanolamide | 7 g |
| Oleyl/cetyl alcohol containing 30 mols of ethylene oxide, marketed under the name MERGITAL OC 30 by HENKEL | 3 g |
| Oleic acid | 20 g |
| Polymer A, 100% of active ingredient | 2 g |
| Benzyl alcohol | 10 g |
| 96° strength ethyl alcohol | 11 g |
| 22° Be strength ammonia solution | 18 ml |
| N,N—Bis-(2-hydroxyethyl)-para-phenylenediamine sulphate | 1 g |
| p-Aminophenol base | 0.4 g |
| Resorcinol | 0.15 g |
| m-Aminophenol base | 0.10 g |
| Alpha-naphthol | 0.40 g |
| Hydroquinone | 0.10 g |
| Ethylenediaminetetraacetic acid | 0.24 g |
| Sodium bisulphite solution (d = 1.32) | 1 ml |
| Water q.s.p. | 100 ml |

30 g of this carrier are mixed in a bowl with 30 g of hydrogen peroxide of 20 volumes strength, containing 0.7% of sodium polyvinylsulphonate. This gives a firm gel which is pleasant to apply and which adheres well to the hair. It is applied with the aid of a paintbrush.

After an interval of 30 to 40 minutes, the hair is rinsed.

The hair is easy to comb out. It has a silky feel. It is set and dried. The hair is shiny and lively and has body (volume); it has a silky feel and is easy to comb out. An ashen deep blond shade is obtained.

Examples 20 to 23 are reducing compositions used for perming or straightening human hair.

EXAMPLE 20

| | |
|---|---|
| Thioglycolic acid | 6.0 g |
| Thiolactic acid | 3.0 g |
| 20% strength ammonia solution | 10.0 g |
| Ammonium bicarbonate | 6.0 g |
| Trilon B* | 0.4 g |
| Polymer A, 100% of active ingredient | 2.0 g |
| Oleyl alcohol polyoxyethyleneated with/20 mols of ethylene oxide | 1.0 g |
| Protein hydrolysate | 0.5 g |
| Perfume, dyestuff, opacifying agent qs, Deionised water q.s.p. | 100 ml |

EXAMPLE 21

| | |
|---|---|
| Sodium bisulphite | 4.0 g |
| Ammonium sulphite | 3.0 g |
| Monoethanolamine | 4.0 g |
| Trilon B* | 0.3 g |
| Polymer A, 100% of active ingredient | 1.0 g |
| Nonylphenol polyoxyethyleneated with 9 mols of ethylene oxide | 1.0 g |
| Perfume | 0.5 g |
| Dyestuff, opacifying agent, q.s. deionised water q.s.p. | 100 ml |

EXAMPLE 22

| | |
|---|---|
| Thioglycolic acid | 7.0 g |
| 20% strength ammonia solution | 6.0 g |
| Monoethanolamine | 1.0 g |
| Ammonium bicarbonate | 3.0 g |
| Masquol DTPA** | 0.5 g |
| Merquat 100 (100% of active ingredient) | 1.0 g |
| Oleyl alcohol polyoxyethyleneated with 20 mols of ethylene oxide | 1.0 g |
| Perfume | 0.5 g |
| Dyestuff, opacifying agent q.s. | 100 ml |
| Deionised water q.s.p. | |

EXAMPLE 23

| | |
|---|---|
| Thioglycolic acid | 5.0 g |
| Ammonium bicarbonate | 5.0 g |
| Masquol DTPA** | 0.3 g |
| Onamer M*** | 2.0 g |
| Oleyl alcohol polyoxyethyleneated with 20 mols of ethylene oxide | 1.0 g |
| Perfume | 0.5 g |
| Dyestuff, opacifying agent q.s. | 100 ml |
| Deionised water q.s.p. | 100 ml |

Examples 24 and 25 are neutralising compositions used for perming or straightening the hair.

EXAMPLE 24

| | |
|---|---|
| Hydrogen peroxide q.s.p. | 8 volumes strength |
| Stabilisers | 0.1 g |
| Sodium polyvinylsulphonate | 1.0 g |
| Citric acid q.s.p. | pH = 3.0 |
| Perfume, peptising agent, opacifying agent, dyestuff q.s. | |
| Demineralised water q.s.p. | 100 ml |

EXAMPLE 25

| | |
|---|---|
| Hydrogen peroxide q.s.p. | 8 volumes strength |
| Stabilisers | 0.1 g |
| Sodium polyvinylsulphonate | 1.0 g |
| Ammonium lauryl-sulphate | 1.0 g |
| Citric acid q.s.p. | pH = 3.0 |
| Perfume, peptising agent, opacifying agent, dyestuff q.s. | |
| Demineralised water q.s.p. | 100 ml |

According to the invention, any one of the reducing compositions from Examples 20 to 23 is applied in a first stage and one of the neutralising compositions 24 or 25 is applied in a second stage, as in the conventional perming processes, after rinsing. A good hold of the perm thus obtained is observed.

| | |
|---|---|
| *Trilon B | Sodium salt of ethylenediaminetetraacetic acid. |
| **Masquol DTPA | Sodium salt of diethylenetriaminepentaacetic acid. |
| ***Onamer M | Poly-(dimethylbutenylammonium chloride)-α,ω-(triethanolammonium chloride) sold by ONYX Chemical Co. |

Polymer A: Cationic polymer consisting of the following repeat units:

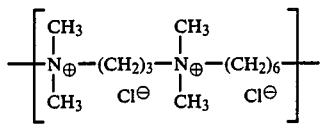

and described in French Pat. No. 2,270,846

EXAMPLE 26

The following composition is prepared:

| | |
|---|---|
| Sodium polyvinylsulphonate | 1 g |
| Polymer sold under the name Cartaretine F8 | 1 g |
| 10° strength ethyl alcohol q.s. | 100 g |

EXAMPLE 27

| | |
|---|---|
| Sodium polyvinylsulphonate | 0.5 g |
| Polymer sold under the name Cartaretine F4 (adipic acid/dimethylaminohydroxypropyl-diethylenetriamine copolymer) | 0.5 g |
| Surface-active agent of the formula: RCHOH—CH$_2$O—[CH$_2$—CHOH—CH$_2$O]—$_n$H R = C$_9$-C$_{12}$ alkyl n is a statistical value equal to 3.5 | 0.5 g |
| 50° strength ethyl alcohol q.s. | 100 g |

EXAMPLE 28

| | |
|---|---|
| Sodium polyvinylsulphonate | 0.25 g |
| Polymer sold under the name Cartaretine F4 | 0.5 g |
| 50° strength ethyl alcohol q.s. | 100 g |

The compositions of Examples 26 to 28 are used for the treatment of the nails. The nails coated with one of these compositions are shiny and hardened.

EXAMPLE 29

The following composition is prepared:

| | |
|---|---|
| Arlacel 165: glycerine monostearate sold by Atlas Powder | 5 g |
| Triple pressed stearic acid | 2 g |
| Tween 60 - sorbitan monostearate oxyethylenated with 20 mols of ethylene oxide sold by Atlas | 1.5 g |
| Cetyl alcohol | 0.8 g |
| Vaseline oil | 20 g |
| Tween 20 - sorbitan monolaurate oxyethylenated with 20 mols of ethylene oxide sold by Atlas | 2 g |
| Glycerine | 7 g |
| Sodium polyvinyl sulphonate | 0.8 g |
| Polymer Jaguar C 13 S | 1 g |
| Preservative | qs |
| Perfume | qs |
| Water | qs |

This composition is used as a rinsing mask after application and allowing to remain. It gives a strengthening effect to the skin.

EXAMPLE 30

The following composition is prepared:

| | |
|---|---|
| Stearic acid | 7.0 g |
| Lanolin | 0.5 g |
| Arlacel 80 - sorbitan mono oleate sold by Atlas | 0.5 g |
| Tween 60 | 2.5 g |
| Sodium polyvinyl sulphonate | 0.3 g |
| Cationic polymer: Jaguar C 153 | 0.5 g |
| Perfume qs | |
| Water and Preservative qs | 100 g |

This composition is a milk having a strengthening effect on the skin.

EXAMPLE 31

The following composition is prepared:

| | |
|---|---|
| Non-auto-emulsifiable glycerol mono- and distearate | 1.2 g |
| MYRJ 49 - polyethylene glycol stearate (20 ethylene oxide units) sold by Atlas | 6.6 g |
| Cetyl alcohol | 4.2 g |
| Mixture of cetostearyl alcohol and sodium alkyl-sulphate | 4.0 g |
| Vaseline oil | 8.0 g |
| Cyclic dimethylpolysiloxane | |
| Preservative | |
| Perfume qs | |
| Sodium polyvinyl sulphonate | 0.3 g |
| JR 400 | 0.5 g |
| Water qsp | 100 g |

This composition is in the form of a cream. It is used for the treatment of greasy skin.

We claim:

1. Process for the cosmetic treatment of hair, which comprises applying a composition which contains 0.01 to 10% by weight of at least one polymer containing one or more cationic groups and selected from a cationic or amphoteric polymer containing primary, secondary, tertiary or quaternary amine units or mixtures thereof and having a molecular weight of 1,000 to 5,000,000 and 0.01 to 10% by weight of at least one anionic polymer containing vinylsulphonic groups of the formula:

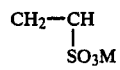

in which M denotes hydrogen, an alkali metal or alkaline earth metal or an ammonium or amine group in a solvent medium which is water, a monoalcohol, a polyalcohol, glycol ether or a mixture thereof.

2. Process according to claim 1, in which after the application of the composition the hair is rinsed with water.

3. Process according to claim 2 in which the polymers are applied as a composition which is in the form of a powder which is mixed with water before application.

4. Process for the cosmetic treatment of hair, which comprises applying first a composition containing 0.01 to 10% by weight of at least one polymer containing one or more cationic groups and selected from a cationic or amphoteric polymer containing primary, secondary, tertiary or quaternary amine units or mixtures thereof and having a molecular weight of 1,000 to 5,000,000 and subsequently a composition containing 0.01 to 10% by weight of at least one anionic polymer containing vinylsulphonic units of the formula:

$$-CH_2-CH-$$
$$|$$
$$SO_3M$$

in which M denotes hydrogen, an alkali metal or alkaline earth metal or an ammonium or amine group in a solvent medium which is water, a monoalcohol, a polyalcohol, glycol ether or a mixture thereof.

5. A composition suitable for application to hair, which contains 0.01 to 10% by weight of at least one polymer containing one or more cationic groups and selected from a cationic or amphoteric polymer containing primary, secondary, tertiary, or quaternary amine units or mixtures thereof and having a molecular weight of 1,000 to 5,000,000 and 0.01 to 10% by weight of at least one anionic polymer containing vinylsulphonic groups of the formula:

$$CH_2-CH-$$
$$|$$
$$SO_3M$$

in which M denotes hydrogen, an alkali metal or alkaline earth metal or an ammonium or amine group, in a solvent medium which is water, a monoalcohol, a polyalcohol, glycol ether or a mixture thereof.

6. A composition according to claim 5, in which each polymer is present in an amount from 0.1 to 5% by weight.

7. A composition according to claim 5, in which M is sodium, potassium, calcium, ammonium or an alkylamine or alkanolamine group.

8. A composition according to claim 5, in which the cationic polymer is:
   (1) a quaternised or unquaternised vinylpyrrolidone/-dialkylaminoalkyl acrylate or methacrylate copolymer,
   (2) a cellulose ether derivative containing quaternary ammonium groups, or a quaternary cellulose derivative,
   (3) a cationic polysaccharide,
   (4) a cationic polymer comprising units of the formula $-A-Z-A-Z-$ (I), in which A denotes a radical containing two amino groups, and Z denotes the symbol B or B', B and B', which are identical or different, denoting a linear or branched alkylene radical which is unsubstituted or substituted by one or more hydroxyl groups and can also contain one or more oxygen, nitrogen or sulphur atoms and/or 1 to 3 aromatic and/or heterocyclic rings;
   or units of the formula: $-A-Z_1-A-Z_1-$ (II), in which A is as defined above and $Z_1$ denotes the symbol $B_1$ or $B'_1$ while denoting the symbol $B'_1$ at least once, $B_1$ denoting a linear or branched alkylene or hydroxyalkylene radical and $B'_1$ denoting a linear or branched alkylene radical which is unsubstituted or substituted by one or more hydroxyl radicals and interrupted by one or more chain nitrogen atoms, the nitrogen atom being substituted by an alkyl chain which optionally contains a chain oxygen atom and optionally contains one or more hydroxyl groups; or
   an alkylation product of a said polymer of formula (I) or (II), which an alkyl or benzyl halide or lower alkyl tosylate or mesylate, or an oxidation product, of a said polymer of formula (I) or (II),
   (5) a polyamino-polyamide,
   (6) a crosslinked polyamino-polyamide which is:
   (a) an optionally alkylated, crosslinked polyamino-polyamide obtained by crosslinking a polyamino-polyamide prepared by the polycondensation of an acid compound with a polyamine, the crosslinking agent being an epihalogenohydrin, diepoxide, dianhydride, unsaturated anhydride or a bis-unsaturated derivative, the crosslinking agent being used in an amount from 0.025 to 0.35 mol per amine group of the polyamino-polyamide;
   (b) a crosslinked polyamino-polyamide obtained by crosslinking a polyamino-polyamide as defined above with a crosslinking agent which is:
   I-a bis-halogenohydrin, bis-azetidinium compound, bis-halogenoacyl-diamine or bis-(alkyl halide);
   II-an oligomer obtained by reacting a compound of group I or an epihalogenohydrin, diepoxide or bis-unsaturated derivative, with a difunctional compound which is reactive towards said compound; or
   III-a quaternisation product of a compound of group I and oligomer of group II, containing tertiary amine groups which can be totally or partially alkylated with an alkylating agent, the crosslinking agent being used in an amount from 0.025 to 0.35 mol per amine group of the polyamino-polyamide; or
   (c) a polyamino-polyamide derivative resulting from the condensation of a polyalkylene-polyamine with a polycarboxylic acid, followed by alkylation by a difunctional agent, said derivatives being of the adipic acid/dialkylaminohydroxyalkyl-dialkylenetriamine copolymer type,
   (7) a polymer obtained by reacting a polyalkylene-polyamine containing two primary amine groups and at least one secondary amine group, with a dicarboxylic acid which is diglycolic acid or a saturated aliphatic dicarboxylic acid having 3 to 8 carbon atoms, the molar ratio of the polyalkylene-polyamine to the dicarboxylic acid being from 0.8:1 to 1.4:1, and the resulting polyamide being reacted with epichlorohydrin in a molar ratio of epichlorohydrin to the secondary amine groups of the polyamide of from 0.5:1 to 1.8:1,
   (8) a cyclic polymer containing units corresponding to the formula:

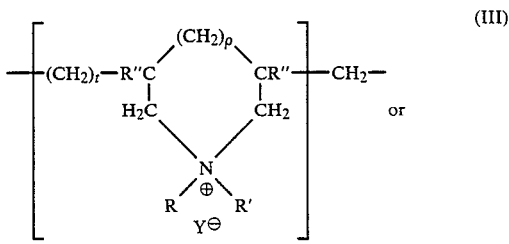

(III)

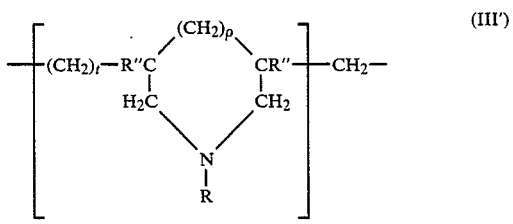

(III')

in which ρ and t are equal to 0 to 1 such that ρ+t=1, R'' denotes hydrogen or methyl, R and R' independently of one another denote an alkyl group having 1 to 22 carbon atoms, a hydroxyalkyl group, or a lower amidoalkyl group, or R and R' together denote with the nitrogen atom to which they are attached, a heterocyclic group, and $Y^\ominus$ is an anion, (9) a poly-(quaternary ammonium) compound of the formula:

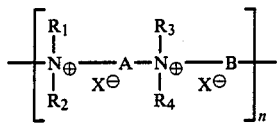
(IV)

in which $R_1$ and $R_2$, and $R_3$ and $R_4$, which are identical or different, represent an aliphatic, alicyclic or arylaliphatic radical containing a maximum of 20 carbon atoms, or a lower hydroxyaliphatic radical, or alternatively $R_1$ and $R_2$, and $R_3$ and $R_4$, together or separately form, with the nitrogen atoms to which they are attached, a heterocyclic ring optionally containing a second heteroatom other than nitrogen, or alternatively $R_1$, $R_2$, $R_3$ and $R_4$ represent a group

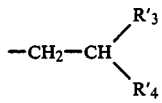

$R'_3$ denoting hydrogen or lower alkyl and $R'_4$ denoting

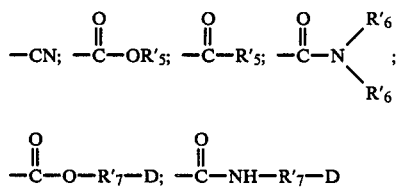

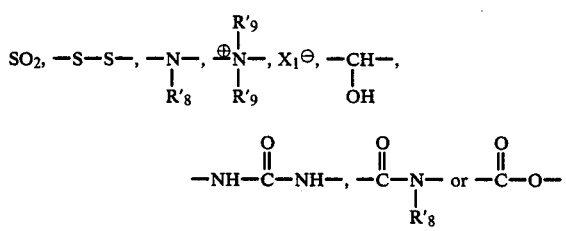

$R'_5$ denoting lower alkyl, $R'_6$ denoting hydrogen or lower alkyl, $R'_7$ denoting alkylene and D denoting a quaternary ammonium group; A and B independently represent a polymethylene group containing from 2 to 20 carbon atoms, which can be linear or branched and saturated or unsaturated and can contain one or more chain aromatic rings, or one or more groups —CH$_2$—Y—CH$_2$—, Y denoting O, S, SO, $$SO_2, -S-S-, -\underset{R'_8}{N}-, -\overset{R'_9}{\underset{R'_9}{\overset{\oplus}{N}}}-, X_1^\ominus, -\underset{OH}{CH}-,$$

$$-NH-\overset{O}{\overset{\|}{C}}-NH-, -\overset{O}{\overset{\|}{C}}-\underset{R'_8}{N}- \text{ or } -\overset{O}{\overset{\|}{C}}-O-$$

$X_1^\ominus$ denoting an anion derived from a mineral or organic acid, $R'_8$ denoting hydrogen or lower alkyl and $R'_9$ denoting lower alkyl, or alternatively A and $R_1$ and $R_3$ form a piperazine ring with the two nitrogen atoms to which they are attached; and, additionally, if A denotes a linear or branched, saturated or unsaturated alkylene or hydroxyalkylene radical, B can also denote a group:

$$-(CH_2)_n-CO-D-OC-(CH_2)_n-$$

in which D denotes:
(a) a glycol radical of the formula —O—Z—O—, in which Z denotes a linear or branched hydrocarbon radical or a group corresponding to the formulae $$-[CH_2-CH_2-O]_{\overline{x}}CH_2-CH- \text{ or}$$

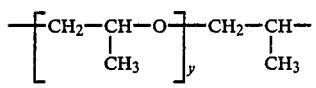

in which x and y independently denote an integer from 1 to 4;
(b) a bis-secondary diamino radical;
(c) a bis-primary diamino radical of the formula: —NH—Y—NH—, in which Y denotes a linear or branched hydrocarbon radical or the radical —CH$_2$—CH$_2$—S—S—CH$_2$—; or
(d) a ureylene group of the formula —NH—CO—NH—; n is such that the molecular weight of the compound is from 1,000 to 100,000; and $X^\ominus$ denotes an anion.

(10) a homopolymer or copolymer derived from acrylic or methacrylic acid and containing at least one unit:

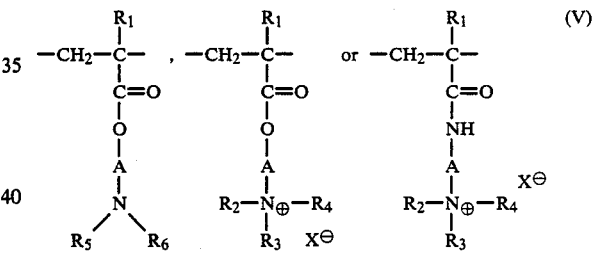
(V)

in which $R_1$ is H or $CH_3$, A is a linear or branched alkyl group having up to 6 carbon atoms or a hydroxyalkyl group having 1 to 4 carbon atoms, $R_2$, $R_3$ and $R_4$, which are identical or different, denote an alkyl group having 1 to 18 carbon atoms or a benzyl group, $R_5$ and $R_6$ independently denote H or alkyl having 1 to 6 carbon atoms and $X^\ominus$ denotes a methosulphate or halide anion, or a crosslinked said copolymer,

(11) a polyalkyleneimine,
(12) a polymer containing one or more chain vinylpyridine or vinylpyridinium units.
(13) a condensate of a polyamine and epichlorohydrin,
(14) a poly-(quaternary ureylene),
(15) a chitin derivative,
(16) a quaternary polymer of vinylpyrrolidone and vinylimidazole, or
(17) a cationic silicone polymer.

9. A composition according to claim 8, in which the cationic polymer is a polymer of group (1), (2), (4), (5), (6), (8), (9), (16) or (17).

10. A composition according to claim 5, in which the polymer containing one or more cationic groups is an amphoteric polymer consisting of units A and B randomly distributed in the polymer chain, with A denoting a unit derived from a monomer containing at least one basic nitrogen atom and B denoting a unit derived from an acid monomer containing one or more carboxylic or sulphonic acid groups, or, alternatively, A and B independently denote groups derived from zwitterionic monomers or carboxybetaine; or A and B independently denote a cationic polymer chain containing secondary, tertiary or quaternary amine groups, in which at least one of the amine groups carries a carboxylic or sulphonic acid group joined via a hydrocarbon radical, or A and B form part of a chain of a polymer containing an alpha, beta-dicarboxyethylene unit in which one of the carboxylic acid groups has been reacted with a polyamine containing one or more primary or secondary amine groups.

11. A composition according to claim 5, which is in the form of an aqueous, alcoholic or aqueous-alcoholic solution, a gel, a thickened lotion, an emulsion, a cream or a powder, optionally as an aerosol.

12. A composition according to claim 5, which contains one or more of a perfume, dyestuff, sequestering agent, thickener, softener, foam synergistic agent, foam stabiliser, sun filter, peptising agent, electrolyte or anionic, cationic, non-ionic or amphoteric surface-active agent or a mixture thereof, in an effective amount.

13. The composition of claim 5 in the form of a shampoo containing a cationic, anionic, non-ionic or amphoteric surface active agent or mixtures thereof, said surface active agent being present in an amount of 3 to 50 percent by weight of said shampoo, said shampoo having a pH of 3 to 10.

14. A composition according to claim 5 in the form of an emulsion selected from the group consisting of (1) nonionic emulsions containing a mixture of oils, a fatty alcohol, or the combination, with a polyoxyethylenated alcohol, (2) mixtures of oils, a fatty alcohol, or combinations thereof, with a polyoxyethylenated alcohol, and a cationic surface active agent, and (3) anionic emulsions containing soap.

15. A composition according to claim 5 in the form of a thickened lotion or gel containing thickening agents selected from the group consisting of sodium alginate, gum arabic, cellulose derivatives, polyethylene glycol stearate, polyethylene glycol distearate and a mixture of an amide and of a phosphoric acid ester, the proportion of thickener comprising 0.05 to 15 percent by weight.

16. A composition according to claim 5 in the form of a styling, shaping, or setting lotion comprising an aqueous, alcoholic, or acqueous-alcoholic solution.

17. The composition of claim 5 in the form of hair dyeing compositions containing an oxidation dyestuff precursor, a direct dyestuff, or mixtures thereof.

18. A composition according to claim 5 in the form of a hair waving or hair straightening composition containing one or more reducing agents.

19. A composition according to claim 5 in the form of a shampoo, lotion, emulsion, gel, or hair waving composition in the form of an aerosol spray.

20. A composition for the cosmetic treatment of hair, which contains 0.01 to 10% by weight of at least one polymer containing one or more cationic groups and selected from a cationic or amphoteric polymer containing primary, secondary, tertiary, or quaternary amine units or mixtures thereof and having a molecular weight of 1,000 to 5,000,000 and 0.01 to 10% by weight of at least one anionic polymer containing vinylsulphonic groups of the formula:

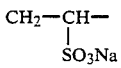

said anionic polymer being a sodium polyvinylsulphonate having a molecular weight of 1,000 to 100,000, in a solvent medium which is water, a monoalcohol, a polyalcohol, glycol ether or a mixture thereof.

21. A composition for the cosmetic treatment of hair, which contains 0.01 to 10% by weight of at least one polymer containing one or more cationic groups and selected from a cationic or amphoteric polymer containing primary, secondary, tertiary, or quaternary amine units or mixtures thereof and having a molecular weight of 1,000 to 5,000,000 and 0.01 to 10% by weight of at least one anionic polymer containing vinylsulphonic groups of the formula:

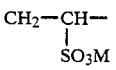

in which M denotes hydrogen, an alkali metal or alkaline earth metal or an ammonium or amine group, said anionic polymer being a copolymer of vinylsulphonic acid and acrylamide, in a solvent medium which is water, a monoalcohol, a polyalcohol, glycol ether, or a mixture thereof.

22. A composition suitable for application to hair, which contains 0.01 to 10% by weight of at least one polymer containing one or more cationic groups and selected from a cationic or amphoteric polymer containing primary, secondary, tertiary or quaternary amine units or mixtures thereof and having a molecular weight of 1,000 to 5,000,000 and 0.01 to 10% by weight of at least one anionic polymer containing vinylsulphonic groups of the formula:

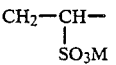

in which M denotes hydrogen, an alkali metal or alkaline earth metal or an ammonium or amine group, and at least one other cosmetically acceptable monomer which is acrylic or methacrylic acid or ester thereof, a substituted or unsubstituted acrylamide or methacrylamide, a vinyl ester, vinyl ether or vinylpyrrolidone, in a solvent medium which is water, a monoalcohol, a polyalcohol, glycol ether, or a mixture thereof.

* * * * *